(12) United States Patent
Rousseau et al.

(10) Patent No.: US 9,687,262 B2
(45) Date of Patent: Jun. 27, 2017

(54) METHODS AND DEVICES FOR TREATING VULNERABLE PLAQUE

(75) Inventors: Robert A. Rousseau, Ottsville, PA (US); Kevin S. Weadock, Hillsborough, NJ (US)

(73) Assignee: Cardinal Health Switzerland 515 GmbH (CH)

( * ) Notice: Subject to any disclaimer, the term of this patent is extended or adjusted under 35 U.S.C. 154(b) by 2595 days.

(21) Appl. No.: 11/290,780

(22) Filed: Nov. 30, 2005

(65) Prior Publication Data
US 2007/0123839 A1 May 31, 2007

(51) Int. Cl.
| | | |
|---|---|---|
| A61M 31/00 | (2006.01) | |
| A61B 17/22 | (2006.01) | |
| A61B 17/00 | (2006.01) | |
| A61B 17/12 | (2006.01) | |
| A61M 25/10 | (2013.01) | |

(52) U.S. Cl.
CPC ........ *A61B 17/22* (2013.01); *A61B 17/12136* (2013.01); *A61B 17/12181* (2013.01); *A61B 17/00491* (2013.01); *A61B 17/12022* (2013.01); *A61B 2017/00893* (2013.01); *A61B 2017/22082* (2013.01); *A61M 25/1002* (2013.01)

(58) Field of Classification Search
CPC .............. A61B 17/22; A61B 17/00893; A61B 17/12136; A61B 17/00491; A61B 17/12181; A61B 2017/22082; A61M 25/1002
USPC .............. 604/96.01, 101.01, 101.03, 101.05, 604/102.01, 102.03, 509
See application file for complete search history.

(56) References Cited

U.S. PATENT DOCUMENTS

| | | |
|---|---|---|
| 4,610,662 A | 9/1986 | Weikl et al. |
| 5,295,962 A | 3/1994 | Crocker et al. |
| 5,464,395 A | 11/1995 | Faxon et al. |
| 5,538,504 A | 7/1996 | Linden et al. |
| 5,554,119 A * | 9/1996 | Harrison ........... A61M 25/1002 604/101.05 |
| 5,611,775 A | 3/1997 | Machold et al. |
| 5,951,458 A | 9/1999 | Hastings et al. |
| 5,993,374 A | 11/1999 | Kick |
| 6,287,320 B1 | 9/2001 | Slepian |
| 6,389,307 B1 * | 5/2002 | Abela ........................... 600/478 |
| 2001/0029349 A1 * | 10/2001 | Leschinsky ............... A61F 2/94 604/101.03 |

(Continued)

FOREIGN PATENT DOCUMENTS

WO   WO 2006/055216 A   5/2006

OTHER PUBLICATIONS

Fujimori, E. "Ultraviolet Light-Induced Change in Collagen Macromolecules", Biopolymers 1965; 3: 115-119.

(Continued)

*Primary Examiner* — Phillip Gray

(57) ABSTRACT

This invention provides methods, devices and kits for treating coronary artery disease, particularly "soft" or vulnerable plaque. The invention is based on the local delivery of crosslinking means to crosslink the collagen covering the plaque and other proteins that may be present at the site to stabilize the plaque and prevent leakage of thrombogenic material into the lumen of the coronary artery. In certain embodiments, catheters are employed to achieve local delivery of a crosslinking agent or ultraviolet light.

4 Claims, 3 Drawing Sheets

(56) References Cited

U.S. PATENT DOCUMENTS

| | | |
|---|---|---|
| 2002/0102645 A1* | 8/2002 | Evans et al. .......... 435/69.1 |
| 2003/0065303 A1 | 4/2003 | Wellman et al. |
| 2003/0163081 A1 | 8/2003 | Constantz et al. |
| 2004/0230156 A1 | 11/2004 | Schreck et al. |
| 2005/0123583 A1 | 6/2005 | Sung et al. |
| 2005/0245893 A1 | 11/2005 | Leschinsky |

OTHER PUBLICATIONS

Miyata, T., et al. "Effects of Ultraviolet Irradiation on Native and Telopeptide Poor Collagen", Biochim Biophys Acata 1971; 229: 672-680.

Weadock, K., et al. "Evaluation of Collage Crosslinking Techniques", Biomaterial Med., Dev., Art. Org., vol. 11, No. 4 pp. 293-318 (1983-1984).

* cited by examiner

METHODS AND DEVICES FOR TREATING VULNERABLE PLAQUE

FIELD OF THE INVENTION

This invention relates generally to treatment of cardiovascular disorders. In particular, the present invention relates to treatment of soft or vulnerable plaque.

BACKGROUND OF THE INVENTION

Myocardial infarction, commonly known as a heart attack, is a major cause of death, disability and healthcare expense in the U.S. and other industrialized societies. For many years, doctors have thought that the main cause of a heart attack or stroke was the buildup of fatty plaque within an artery leading to the heart or brain. With time, the plaque buildup would narrow the artery so much that the artery would either close off or become clogged with a blood clot. The lack of oxygen-rich blood to the heart would then lead to a heart attack. But these types of blockages cause only a portion of the total number of heart attacks.

Researchers are now finding that many people who have heart attacks do not have arteries severely narrowed by plaque. In fact, vulnerable plaque may be buried inside the artery wall and may not always bulge out and block the blood flow through the artery. It is now believed that "soft" or vulnerable plaque is formed in the artery wall. More specifically, fat droplets are absorbed by the artery wall, which causes the release of cytokines that lead to inflammation. The cytokines make the artery wall sticky, which attracts monocytes. The monocytes squeeze into the artery wall. Once inside, the monocytes turn into macrophages and begin to soak up fat droplets. The fat-filled cells form a plaque with a thin covering made of collagen, typically type I collagen. Inflammation can predispose the thin collagen layer covering the plaque to crack, spilling the contents of the plaque into the bloodstream. The sticky cytokines on the artery wall capture blood cells (mainly platelets) that pass by the site. When these cells clump together, they can form a clot large enough to block the artery.

Current treatments for coronary artery disease include the use of stents, angioplasty, rotational atherectomy, cutting balloons, pharmaceutical agents, and lasers. However, these methods and devices are directed to treatment of hard atherosclerotic plaque and would not be effective in treating soft or vulnerable plaque. At this time no known treatment for vulnerable plaque exists. Therefore, there is a need for methods and devices to treat vulnerable plaque.

SUMMARY OF THE INVENTION

The present invention provides methods, devices, and medical kits useful for treating vulnerable plaque. More specifically, the methods and kits of the present invention are based on delivery of a crosslinking means to the collagen layer covering the plaque. Crosslinking of the thin collagen lining covering vulnerable plaque stabilizes the lining and reduces the likelihood of leakage of thrombogenic material into the lumen of the coronary artery.

In one aspect, the present invention provides methods for treating vulnerable plaque through the delivery of a chemical crosslinking agent via specialized catheters. Crosslinking agents refer to compounds that crosslink proteins such as collagen. Examples of suitable crosslinkers include aldehydes (e.g., glutaraldehyde, formaldehyde), isocyanates, carbodiimides, alkyl and aryl halides, and imidoesters.

In a specific embodiment, a crosslinking agent is delivered through a catheter that permits the selected part of the artery to be bathed in the crosslinking solution without interrupting blood flow. An example of this type of catheter is illustrated in FIG. 2.

In another embodiment, a crosslinking agent is delivered through a catheter designed to have a sponge tip at the distal end of the catheter. The sponge tip is in fluid communication with the lumen within the shaft of the catheter, and the delivery of a crosslinking agent to the sponge tip is accomplished by perfusing the sponge with the agent via the lumen. The sponge can be made of a material that is biocompatible and hydrophilic, such as crosslinked hydrogels. The sponge tip provides good contact with the collagen layer as well as limit diffusion of the crosslinking agent to other tissue sites. An example of this type of catheter is illustrated in FIG. 3.

In still another embodiment, a crosslinking agent is delivered through a dual balloon catheter.

In a further embodiment, catheter systems designed for embolic protection are utilized in practicing the methods of the present invention.

In an additional embodiment, the catheter employed for the local delivery of a crosslinking agent is adapted to be used in conjunction with an imaging guide wire that essentially provides in situ images of a vulnerable plaque.

In another embodiment, a crosslinking agent is encapsulated in microcapsules that are disposed on the outer surface of an expandable balloon mounted at the distal end of the catheter. These capsules are ruptured during expansion of the balloon and subsequent compression against the collagen layer of the vulnerable plaque. This compression results in release and local delivery of the crosslinking agent.

Other therapeutic agents may also be added to other microcapsules adhered to the balloon. Such agents include anti-thrombotics and antiplatelet drugs such as aspirin, clopidogrel, ticlopidine, and dipyridamole. Other drugs that may provide particular benefit to the diseased region by such a mode of delivery include GPIIb/IIIa inhibitors, sirolimus, paclitaxel, and anti-coagulants such as warfarin (also known as Coumadin®), heparin, and enoxaparin (also known as Lovenox). Another drug that may help the patient by this form of delivery is recombinant tissue plasminogen activator (rt-PA), a genetically engineered form of t-PA, a thombolytic substance made naturally by the body.

In still another embodiment, the present invention provides kits containing a catheter and a crosslinking agent suitable for treating vulnerable plaque.

In a further aspect of the present invention, crosslinking of the thin collagen lining covering vulnerable plaque is achieved through the use of ultraviolet light. Ultraviolet is known to crosslink collagen (Fujimori E, *Ultraviolet light-induced change in collagen macromolecules*, Biopolymers 1965; 3: 115-119; Miyata T, Sohde T, Rubin A L, Stenzel K H., *Effects of ultraviolet irradiation on native and telopeptide-poor collagen*, Biochim Biophys Acta 1971; 229: 672-680). UV light can be provided by light emitting catheters with micro light emitting diode (LED) arrays on their distal end, or applied by a surgeon to the exterior of the vessel at the location of the plaque during surgery by use of a fiber optic carrying the UV light.

DETAILED DESCRIPTION OF THE INVENTION

Figure 1:
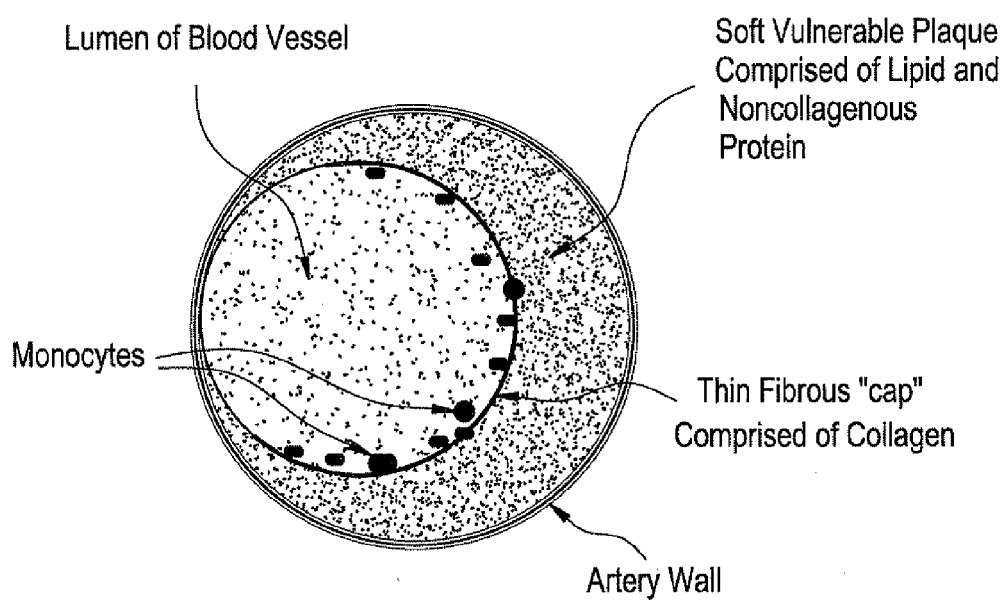
FIG. 1 illustrates the process of vulnerable plaque formation. Inflammation may cause the thin collagen covering over the plaque to crack, spilling the contents of the artery into the bloodstream. The sticky cytokines on the artery wall capture blood cells (mainly platelets) that rush to the site of injury. When these cells clump together, they can form a clot large enough to block the artery

The present invention is directed to treatment of vulnerable plaque.

Vulnerable plaque is formed in the wall of an artery wherein a core of lipid-rich cells is covered by thin layer of collagen. These vulnerable plaques are prone to rupture and erosion, which results in spilling of the contents of the artery into the bloodstream and subsequent formation of thrombi in the artery. These thrombi may grow rapidly and block the artery, or detach and travel downstream, leading to embolic events, unstable angina, myocardial infarction, or sudden death.

The present invention provides methods, devices, and kits for treating vulnerable plaque based on delivery of a crosslinking means to the vulnerable plaque. According to the present invention, the crosslinking means causes crosslinking of collagen, typically type I, which is the main protein component of the thin lining covering vulnerable plaque. The crosslinking means may also cause crosslinking of other proteins that may be present in the plaque, such as fibrin, thrombin, fibrinogen, immunoglobulins, albumin, and hemoglobin. Such crosslinking stabilizes the plaque and prevents the plaque lining from rupturing due to shear forces or enzymatic degradation by matrix metallo-proteinases (MMP).

According to the present invention, suitable crosslinking means include both chemical means such as chemical crosslinking agents, and physical means such as ultraviolet light (200-400 nm), preferably 240-300 nm, and more preferably 254 nm.

In a specific aspect of the present invention, a crosslinking agent is employed for treating vulnerable plaque.

The term "crosslinking agent" refers to a compound that crosslinks proteins, particularly collagen. Protein crosslinkers are well known in the art and many are commercially available. Suitable crosslinking agents include bi-functional reagents containing reactive groups that form bridges between two amino acid side chains of adjacent protein molecules. Examples of such reagents include aldehydes (e.g., glutaraldehyde, formaldehyde), isocyanates, carbodiimides, alkyl and aryl halides, and imidoesters. A single crosslinking agent or a combination of several crosslinking agents can be administered to the site of vulnerable plaque.

A crosslinking agent can be delivered to the site of vulnerable plaque by various means. In one embodiment, a crosslinking agent is delivered locally to the region of vulnerable plaque by using a catheter.

Catheters and their use in delivery of pharmaceutical agents to the interior of blood vessels have been well documented in the art. See, U.S. Pat. No. 5,295,962, U.S. Pat. No. 5,464,395, U.S. Pat. No. 5,538,504, U.S. Pat. No. 5,611,775 and U.S. Pat. No. 5,951,458, for example. Catheter-based local or regional delivery offers a number of advantages over a systemic delivery and delivery via an implantable medical device. For example, a relatively high tissue concentration may be achieved by the direct deposition of a desired agent in the arterial wall. Local delivery through a temporarily inserted catheter eliminates the potential side affects associated with a permanently implanted device, such as inflammatory reaction and long term tissue damage. It should be noted, however, that a catheter-based local delivery can be utilized in combination with drug eluting stents or other coated implantable medical devices.

Figure 2:
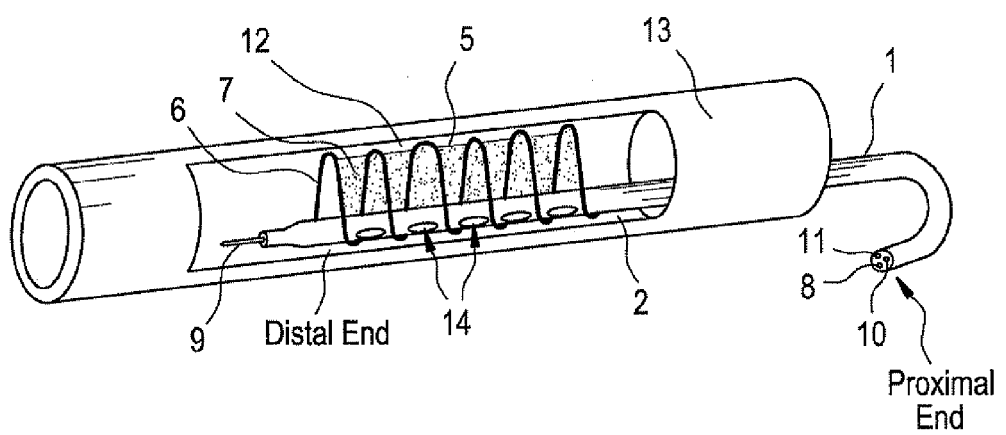
FIG. 2 is a schematic drawing of a Dispatch™ catheter.

In a preferred embodiment, delivery is achieved via a catheter that allows local delivery of a solution containing the crosslinking agent to the arterial region with vulnerable plaque without interrupting blood flow. FIG. 2 depicts an example of such a catheter, which is also commercially available under the trade name of "Dispatch™ catheter". The catheter 1 comprises an elongate tubular body 2 for extending between a proximal control end 3 and a distal function end 4. The distal end 4 of the catheter 1 has an inflatable balloon 5, which is composed of a spiral inflation coil 6 wrapped around a sheath 7. The tubular body 2 of the catheter is designed to have a guide wire lumen 8 adapted to slidably accommodate a guide wire 9 extending therethrough, an inflation lumen 10 that is in fluid communication with the interior of the balloon 5, and a delivery lumen 11 for delivering aqueous solutions. In the present invention, the delivery lumen is used to deliver aqueous solutions of crosslinking agents. The guide wire 9 is typically formed out of a strong flexible wire such that it can be passed through various bodily passageways to reach a remote site within a patient's body.

In practice, the guide wire 9 is positioned near a site to be treated. The catheter 1 can then be advanced over the guide wire 9, positioning the inflatable balloon 5 near the treatment site. Inflation means such as a saline or gas can then be supplied via the inflation lumen, inflating the balloon 5 to form a tube or delivery chamber 12 through which blood can flow. In addition, inflation brings the spiral coil in contact with the luminal surface of the arterial wall such that the coil and the artery 13 form the walls of the delivery chamber 12, wherein the solution of a crosslinking agent can be infused through the delivery lumen and enters the delivery chamber via delivery ports 14. The guide wire 9 can be withdrawn proximally out of the catheter, either before or after balloon inflation. The spiral balloon 5 serves to center the delivery chamber 12, useful when the balloon is inflated in vessel curves or bends. It should be understood, however, that the balloon may take other forms, such as a serpentine shape or a toroidal-serpentine shape, so long as the catheter permits local delivery without interrupting blood flow. See U.S. Pat. No. 5,951,458 for such additional balloon constructions, the teaching of which is incorporated herein by reference.

The amount of crosslinking agent(s) delivered should be effective to cause crosslinking of the collagen covering the vulnerable plaque contents. Generally speaking, 0.1-2.0 ml of a solution is delivered, which should contain crosslinking agent(s) at a total concentration of 0.1% to 4% (w/v), preferably 0.1% to 1% (w/v), and more preferably 0.3% to 0.5% (w/v). The concentration of crosslinking agents can be adjusted depending on the particular crosslinking agent(s) being used. Delivery can be performed as several infusions, for example, 2 or 3 infusions, over the course of 2-3 minutes. Generally speaking, the amount of time required for sufficient crosslinking is inversely related to the concentration of the crosslinking agent used. After the last infusion, the site can be rinsed with saline to dilute residual crosslinking agents. Glycine can be added to the saline to sequester residual crosslinking agents that react with amine groups, e.g., aldehydes. Thereafter, the inflation coil is deflated and the catheter is gently removed.

Preferred concentrations and durations of exposure of the crosslinking agent to the vulnerable plaque can be predetermined in vitro. A variety of crosslinking strategies can be available for a given catheter type or vulnerable plaque lesion. The exact regimen can be selected by the physician prior to treating the patient. The selection is based on previously conducted in vitro experiments involving exposure of blood vessels to selected crosslinking agents. The selection would be based on data extracted from experiments that varied concentration of the crosslinking agent, pH, temperature, and duration of treatment. Such in vitro evaluations of crosslinking agents on collagen films have been previously described (Weadock et al., Evaluation of Collagen Crosslinking Techniques, *Biomat. Med. Dev. Art. Org.* 11(4): 293-318 (1983-1984)) and are known to others skilled in the art of evaluating collagen crosslinking.

In those instances where a side branching coronary vessel is located between the balloons of the catheter, it is preferable to use the sponge tipped embodiment or physical means such as UV light to crosslink the collagen covering the vulnerable plaque. These two modes of crosslinking, as further described hereinbelow, prevent or reduce the likelihood of crosslinking agent affecting non-target (non-diseased) tissue. Alternatively, a coronary sinus catheter can be used simultaneously along with the catheters of the present invention to capture residual crosslinking agent and prevent it from entering the systemic circulation.

Figure 3A:
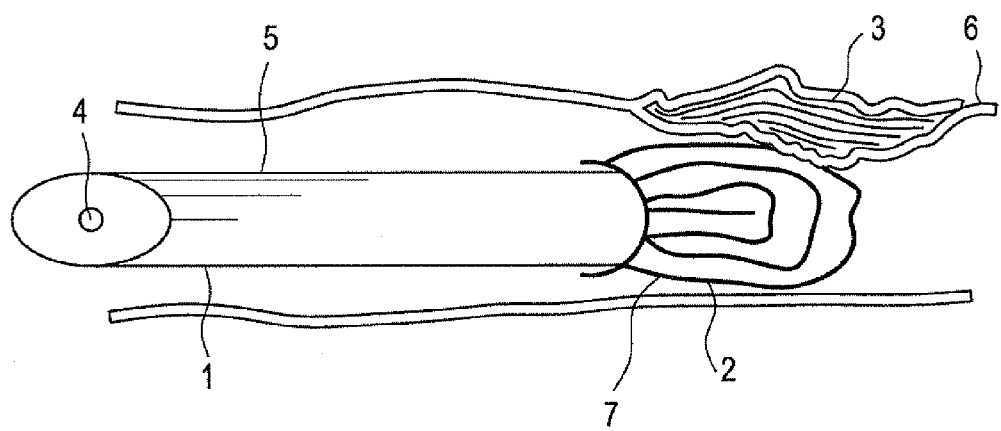
FIG. 3 is a schematic drawing of a catheter with a sponge tip.
Figure 3B:
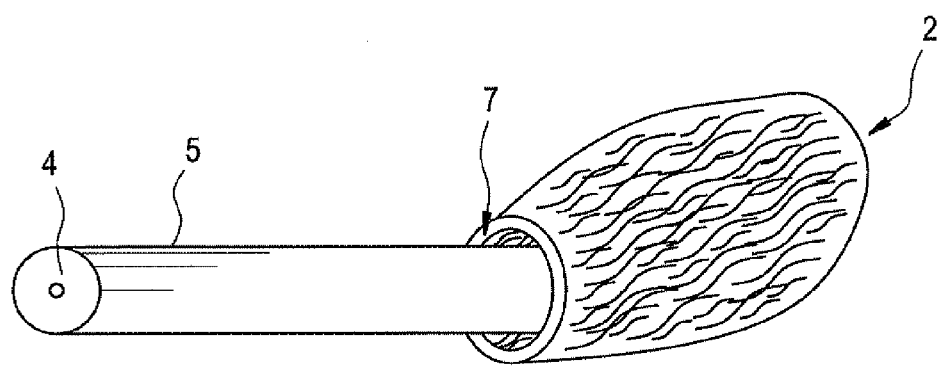

In another embodiment, a crosslinking agent is delivered through a catheter designed to have a sponge tip. FIG. 3 illustrates this embodiment of the present invention. As shown in FIG. 3, catheter 1 has a sponge tip 2 at the distal end of the catheter, attached to the catheter via an attachment means 7. Sponge tip 2 is in fluid communication with lumen 4 within the shaft 5 of the catheter. Catheter 1 is inserted into the lumen of an artery and is passed down means that guides the catheter to the site of vulnerable plaque 3. The vulnerable plaque is surrounded by a thin capsule 6 of collagen. The delivery of a suitable crosslinking agent to sponge tip 2 is accomplished by perfusing the sponge with the agent via lumen 4. Exposure to fluid causes the sponge to swell and engage the collagen in the vessel wall at the site of the vulnerable plaque. The sponge can be held within a chamber or non-swollen condition within a cavity present at or near the distal end of the catheter. A blocking sponge or balloon can also be used to prevent distal migration. A catheter with a sponge tip provides targeted delivery of a crosslinking agent to the surface of vulnerable plaque with favorable diffusability and avoids having excess crosslinking agent delivered to unaffected tissues.

The sponge can be made of a material that is biocompatible, highly compliant, atraumatic to the lumenal surface, and hydrophilic. Suitable materials for making the sponge include crosslinked hydrogels. Hydrogels are a class of hydrophilic polymers which swell in the presence of aqueous solutions to form an elastic gel matrix. Both polyacrylamide-based hydrogels and polyurethane-based hydrogels can be used to make the sponge tip of catheters and have been described in the art. For example, suitable hydrogels can be made from polyethylene glycol (PEG), polyacrylamide, sodium or calcium alginate, hyaluronic acid, the GANTREZ™ group of polymers, gelatin, poly-hydroxyethylmethacrylate (pHEMA), poly-methylmethacrylate (PMMA), silicone, and thermo-reversible gel systems derived from polysaccharides, starch, and pectin, among others.

Attachment of the sponge to the catheter is accomplished by using an attachment means such as an adhesive, e.g., a cyanoacrylate or other strong adhesive. The sponge can also be attached by mechanically crimping the sponge to the catheter with a band made of a biocompatible metal or polymer, preferably a radio-opaque material. Suitable metals and polymers are known to those skilled in the art of catheter manufacture.

Where a catheter with a sponge tip is employed for delivery, 1-3 ml of a solution containing one or more crosslinking agents is delivered, which should contain crosslinking agent(s) at a concentration of 1% to 15% (w/v), preferably 3% to 5% (w/v). Delivery can be performed as several infusions, for example, 2 or 3 infusions, over the course of 1-10 minutes.

In a further embodiment, a crosslinking agent is delivered through a dual balloon catheter. Dual balloon catheters have been described in the art, e.g., in U.S. Pat. No. 4,610,662 and U.S. Pat. No. 6,287,320, the teachings of which are incorporated herein by reference. A dual balloon catheter typically has two members expansible to produce a chamber between the two members. The catheter is introduced into a vessel and is positioned such that the two expansible members are disposed on opposite sides of the vulnerable plaque. The interior of the two expansible members is in fluid communication with an inflation lumen in the catheter. Inflation means such as a saline or gas can be supplied via the inflation lumen to inflate the two members and isolate the region with the plaque. A crosslinking solution is then introduced via a delivery lumen in the catheter into the chamber formed between the two members. The catheter can also include a central balloon between the two expansible members to assist in delivering the crosslinking solution into the plaque by increasing the pressure between the two balloons. Delivery by a dual balloon catheter is chosen when there are no arterial branches between the balloons. In those instances where a side branching coronary vessel is located between the balloons of the catheter, it is preferable to use the sponge tipped embodiment or physical means such as UV light to crosslink the collagen covering the vulnerable plaque. These two modes of crosslinking prevent or reduce the likelihood of crosslinking agent affecting non-target (non-diseased) tissue. In addition, the extent of disease may preclude the use of a dual balloon catheter since diffusion of agent through the lesion may be impaired or difficult to control.

Where a dual balloon catheter is employed for delivery, 1-3 ml of a solution containing crosslinking agents is delivered, which should contain crosslinking agent(s) at a concentration of 1% to 15% (w/v), preferably 3% to 5% (w/v). Delivery can be performed as several infusions, for example, 2 or 3 infusions, over the course of 1-10 minutes.

In a further embodiment, catheter systems designed for embolic protection are utilized in practicing the methods of the present invention. For example, the ANGIOGUARD™ Emboli Capture Guidewire (Cordis Corporation, Florida) is an embolic protection filter, which opens into a tiny protective basket designed to catch plaque particles dislodged during a procedure. After the completion of a procedure (e.g., the delivery of a crosslinking agent), the basket is collapsed and can be pulled back through the catheter. Thus, the ANGIOGUARD™ Emboli Capture device may be used during the treatment of vulnerable plaque with crosslinking agents such that the residual crosslinking agents or emboli that might be generated during the procedure can be captured.

Another embolic protection device, the TriActiv® System, is available from Kensey Nash Corporation, Exton, Pa. The TriActiv® System is designed to prevent distal embolization during vein graft interventions and reduces the potential for associated adverse coronary events. This is accomplished with three integrated system features: a protection balloon, active flushing, and an automated extraction system to remove problematic debris from the treated vessel. A crosslinking agent can be delivered by using the Tri-Activ® System.

In another embodiment, an aqueous solution containing one or more crosslinking agents are encapsulated in microcapsules adhered to the outer surface of an expandable balloon mounted at the distal end of a catheter. The adhesion can be achieved by using an adhesive such as a cyanoacrylate or acrylic adhesive. These capsules are ruptured during expansion of the balloon, as the microcapsules are compressed against the vulnerable plaque and the crosslinking agents are thereby released and locally delivered to the thin collagen layer covering the vulnerable plaque. Microcapsules encapsulating aqueous solutions can be made using methods known to those skilled in the art. See, for example, U.S. Pat. No. 5,993,374.

In an additional embodiment, the catheter employed for the local delivery of a crosslinking agent, such as any one of those catheters described hereinabove, is adapted to be used in conjunction with an imaging guide wire that essentially provides in situ images of a vulnerable plaque. An example of an imaging guide wire is that developed by Lightlab Imaging (Westford, Mass.), which can identify structural features of vulnerable plaques based on optical coherence tomography (OCT). OCT uses infrared light waves that reflect off the internal microstructure within the biological tissues. The frequencies and bandwidths of infrared light are orders of magnitude higher than medical ultrasound signals, resulting in greatly increased image resolution. Infrared light is delivered to the imaging site through a single optical fiber of a 0.006" in diameter. The imaging guide wire contains a complete lens assembly to perform a variety of imaging functions.

The catheters of the present invention can be adapted to be used with the guidewire by having a lumen through which the guidewire is placed. Alternatively, the catheters of the present invention can be modified to incorporate features for "rapid exchange". Rapid exchange-catheters are constructed so that the guide wire passes only through the distal portion of the catheter. Rapid exchange catheters enable procedures that can be performed solely by the physician, eliminating the need for a nurse or resident assistant.

The present invention also provides kits containing a catheter and a crosslinking agent as described hereinabove, wherein the catheter is designed to deliver the crosslinking agent locally to treat vulnerable plaque. The kits can contain other components such as syringes, stopcocks, and tubing for facilitating transport of the crosslinking agent into the catheter.

In another aspect of the present invention, crosslinking of the thin collagen layer over the plaque can be achieved through the use of physical means, for example, ultraviolet light.

In one embodiment, catheters with micro light emitting diodes (LED) arrays on their distal end, which arrays emit UV light having a wavelength of 200-400 nm, preferably 254 nm, are employed to cause crosslinking of collagen. Light emitting catheters with micro LED arrays on their distal end that are covered with a balloon can be made using techniques known in the art. Preferably, the light source is enclosed within a balloon made of a material that is substantially transparent to wavelengths of 200-400 nm. When the balloon is expanded at a site covering the vulnerable plaque, the light is emitted. The use of a balloon allows for the elimination of blood from the treatment site and reduction of any absorption effects the blood might present. In a preferred embodiment, the plaque is illuminated with UV light of approximately 0.1-10 Watts for 1-10 minutes.

In another embodiment, a UV light source can be applied by a surgeon directly to the location of the plaque during coronary artery bypass surgery (CABG) for about 5 minutes. The present methods allow a surgeon or interventional cardiologist to treat vulnerable plaque without the use of stents, angioplasty, or CABG surgery. However, the methods of the present invention can also be used in concert with existing treatment of coronary diseases, i.e., stents and angioplasty, for example.

What is claimed is:
1. A method for treating vulnerable plaque, comprising:
positioning an intraluminal catheter proximate a vulnerable plaque lesion, the intraluminal catheter comprising an inflatable balloon consisting of a spiral inflation coil wrapped around a sheath and a distal section of the catheter coextensive with said spiral inflation coil with multiple delivery ports in fluid communication with a delivery lumen; and
delivering at least one crosslinking agent locally to said vulnerable plaque lesion, including manipulating the intraluminal catheter such that upon inflation of the balloon to bring said spiral inflation coil into direct contact with the vulnerable plaque lesion a plurality of delivery regions are formed by gaps created between the delivery ports and the vulnerable plaque lesion, wherein each delivery region is formed by adjacent turns of said spiral inflation coil and is in fluid communication with at least one of said multiple delivery ports, for the delivery through the ports of the crosslinking agent to the vulnerable plaque lesion.

2. The method of claim 1, wherein said crosslinking agent crosslinks a collagen component of said vulnerable plaque.

3. The method of claim 1, wherein said crosslinking agent is selected from a group consisting of aldehydes, isocyanates, carbodiimides, alkyl and aryl halides, and imidoesters.

4. The method of claim 3, wherein said aldehydes are selected from glutaraldehyde or formaldehyde.

* * * * *